United States Patent [19]

Gould et al.

[11] Patent Number: 4,676,985

[45] Date of Patent: Jun. 30, 1987

[54] ECOLOGICALLY IMPROVED PROCESS OF PROTECTING CERTAIN CROPS FROM DAMAGE BY SOIL-INHABITING INSECT PESTS AND PRODUCT PRODUCED THEREBY

[75] Inventors: Fred L. Gould, Raleigh, N.C.; Diana C. Pour, Cincinnati, Ohio; Michael G. Villani, Bethel, Minn.

[73] Assignee: North Carolina State University, Raleigh, N.C.

[21] Appl. No.: 624,586

[22] Filed: Jun. 26, 1984

[51] Int. Cl.⁴ .............................................. A61K 35/78
[52] U.S. Cl. .......................... 424/195.1; 424/DIG. 12; 514/919
[58] Field of Search .................... 424/195.1, DIG. 10; 47/57.6; 514/919

[56] References Cited

FOREIGN PATENT DOCUMENTS 954015  5/1982  U.S.S.R. ................................ 47/57.6

OTHER PUBLICATIONS

J. H. Comstock and M. V. Slingerland, *Wireworms*, Bulletin 33 of the Cornell University Agricultural Experiment Station (1891).

J. R. Dogger and J. H. Lilly, *Journal of Economic Entomology* 42, 663 (1949).

L. M. Schoonhoven, *Ent. Exp. & Appl.* 31, 57 (1982).

Katsura Munakata, *Insect Feeding Deterrents in Plants*, Chapter 6 of the Laboratory of Pesticides Chemistry Faculty of Agriculture, Nogoya University (1977).

T. Jermy, *Acta Phytopathologica Academiae Scientiarum Hungaricae* 6, 253 (1971).

C. H. Brett, *Scientific Notes*, Repellent Properties of Extract of *Amorpha fruticosa*, 810 (1946).

R. F. Chapman, *Bull. Ent. Res.* 64, 339 (1974).

*Primary Examiner*—Johnnie R. Brown
*Assistant Examiner*—John W. Rollins
*Attorney, Agent, or Firm*—Bell, Seltzer, Park & Gibson

[57] ABSTRACT

A process of protecting certain crops from damage by soil-inhabiting insect pests and product produced thereby are disclosed in which seed or seedlings are coated with a plant extract having a natural feeding deterrency of predetermined efficacy to such insect pests and which has no appreciable phytotoxicity to the seeds or seedlings. More specifically, such seeds or at least the below-ground portions of seedlings are coated with an extract from a plant selected from the group consisting of butterfly milkweed, English ivy, santolina, bergamot, clary and swamp milkweed.

17 Claims, No Drawings

ECOLOGICALLY IMPROVED PROCESS OF PROTECTING CERTAIN CROPS FROM DAMAGE BY SOIL-INHABITING INSECT PESTS AND PRODUCT PRODUCED THEREBY

The present invention relates to the protection of certain crops from soil-inhabiting insects and more particularly to an ecologically improved process of protecting seeds and young seedlings from damage from soil-inhabiting insect pests which would otherwise damage the seeds or seedlings and to the seeds and seedlings produced thereby.

BACKGROUND OF THE INVENTION

Soil-inhabiting insects cause damage to certain crops resulting in estimated losses of many millions of dollars each year. For example, wireworms and southern corn rootworms have been estimated to cause losses of 46 million dollars per year and 11 million dollars per year, respectively, in the Southeast alone (ESA Southeastern Branch, Insect Detection, Evaluation and Prediction Report, 1981). Present techniques for controlling these pests rely almost exclusively on soil insecticides which are very expensive (costing as much as 15 to 20 dollars per acre) and have the potential of having adverse ecological and environmental effects.

Certain plants have evolved rather potent chemical defenses which deter feeding by certain insects and it has been suggested previously that such natural feeding deterrents might be used in crop pest management. However, the results from previous attempts to use such deterrents for the control of insects have been poor. Reasons given for this lack of success include phytotoxicity, lack of persistence, socio-economic constraints, and the inability to duplicate laboratory results in the field. Such unsuccessful attempts to use natural feeding deterrents have resulted in the promulgation of suggested sets of criteria that potential feeding deterrents must meet to receive serious consideration for use in the field. Among these criteria are: adequate persistence for crop protection, systemic activity, low cost, and lack of phytotoxicity. While these suggested sets of criteria may have increased the efficiency of screening for effective deterrents, they have not resulted, to our knowledge, in any current commercial use of natural deterrent compounds in the field for crop pest management.

We believe the main reason for the lack of success in the use of natural feeding deterrents for crop pest management is that such prior attempts have focused mainly on the protection of plant foliage and fruit. These attempts at protecting plant foliage and fruit may have been unsuccessful because (1) persistence is needed for extremely long periods of time (2) a high degree of systemic action is needed, and (3) large quantities of the deterrent are needed to treat the foliage and fruit.

With the foregoing in mind, it is an object of the present invention to provide effective crop pest management using natural feeding deterrents which has the required persistence and low cost and in which the need for systemic action is decreased.

A more particular object of the present invention is to provide effective crop pest management by protecting seeds and the below-ground portions of seedlings from damage from certain soil-inhabiting insect pests through the use of plant extracts which are effective feeding deterrents against those soil-inhabiting insect pests which would otherwise damage the seeds or seedlings.

SUMMARY OF THE INVENTION

These objects of the present invention are accomplished by coating seeds or seedlings of those crops, which are particularly susceptible to damage from certain soil-inhabiting insect pests, with extracts from those plants which produce natural feeding deterrents effective as to those soil-inhabiting insect pests. Specifically, corn seeds have been shown to be protected from corn wireworm by extracts from butterfly milkweed, English ivy, santolina, bergamot, clary and swamp milkweed while these seeds are protected from southern corn rootworms by extracts from the first three of the above listed plants.

DESCRIPTION OF THE PREFERRED EMBODIMENTS

The plant extracts providing the insect feeding deterrents which have been found effective can be produced by collecting specimens of the plants, grinding the plant specimens and then pressing the ground plant material to force the liquid therefrom. Specifically, the plant specimens were homogenized in a blender or meat grinder without solvent within six hours of collection. Liquid from each homogenate was extracted with a hydrolytic press and immediately frozen and stored at −20° C. until needed for use.

Certain parts of some plants and other plants during certain phases in their growth cycle present phytotoxicity problems. It is important to avoid any significant phytotoxicity while still achieving protection of the seeds or seedlings.

Of the plants which we have found to be effective as producing feeding deterrents, several present potential phytotoxicity problems and care must be taken in the collection and handling thereof. Both butterfly and swamp milkweed should be collected only after peak flowering to avoid phytotoxicity. With these plants, collection is preferably accomplished by cutting the plants at ground level. Cut plants should be kept cool until processed and this is preferably accomplished by storing the cut plants in a cooler at 45° F.

Processing should be done within 6 hours of collection and is accomplished by stripping the leaves and flowers from the stems of the butterfly and swamp milkweed plants (*Asclepsias tuberosa* and *Asclepsias incarnata*, respectively). The leaves and flowers are then homogenized in a meat grinder or blender and then pressed in a mechanical press to extract liquid therefrom. The extract is immediately frozen and may be stored at −20° C. for at least two years before use.

English ivy (*Hedera helix*) may be collected at any time during spring and summer, but only new shoots and leaves should be collected from the plants to maximize efficiency of extract collection. Storage and processing is done the same as with the butterfly and swamp milkweed.

Santolina (*Santolina virens*) is collected by pruning cultivated plants at any time of year. The stems, leaves and flowers pruned from the plants are stored and processed the same as the milkweed.

Individual leaves may be picked from clary (*Salvia sclera*) any time of year and stored and processed the same as milkweed. Only intact leaves should be processed to produce the extract.

Bergamot (Monarda sp.) is collected, stored and processed the same as clary except that the entire plant is processed.

The extracts from English ivy, santolina, clary and bergamot may be stored frozen for at least one year at −20° C. before use. This facilitates collection at appropriate times and processing for use during the planting season.

When it is desired to prepare seeds for planting, a selected extract is thawed and brought to room temperature. The seeds are then coated in any suitable manner, such as by spraying, dipping, etc., until each entire seed is thoroughly coated with extract. Any excess extract is recovered for reuse. The coated seeds are then air-dried until the coating is completely dry, such as for example two hours at ambient temperature. Experiments have shown that the thusly coated seeds may be held for at least two days before planting and other evidence suggests that they may be held for several weeks before planting with no appreciable loss of protection.

Seedlings are protected when they reach transplant stage. The seedlings are uprooted and any excess soil is removed. The main below-ground portion of the stem of each seedling is then coated with extract, such as by spraying, dipping, etc., until thoroughly coated. When the extract is applied by spraying, filtered extract should be used and the extract should be applied to run off. Excess extract should be collected and reused. The coated seedlings are then transplanted into the field by conventional techniques.

Seed corn has been coated with extracts from each of the plants described above. Tests were conducted to determine feeding deterrency with both corn wireworms and southern corn rootworms. Butterfly milkweed, English ivy and santolina were effective as to both corn wireworms and southern corn rootworms, but bergamot, clary and swamp milkweed were effective only as to corn wireworms.

Seed corn treated with crude extract collected from butterfly milkweed plants without attention to flowering period exhibited slight phytotoxicity in the form of delayed germination and depressed growth rates. The delay in germination is small (0.52 days) as was the depressed growth rates (6% smaller after 21 days). Experiments have indicated that dilution of this extract (e.g. 0.5 concentration) overcomes this phytotoxicity. Additional experiments using full strength extract collected after peak flowering indicate no phytotoxicity.

It is believed that these extracts will be similarly effective in protecting a variety of seeds. Similarly, while extracts of the above listed plants were determined to be effective as to corn wireworms and southern corn rootworms, it is believed that extracts from other plants in the same genre may be found which would be effective as to these insect pests. Further, it is expected that these extracts may provide natural feeding deterrents to other soil-inhabiting insect pests.

In the specification, there have been set forth preferred embodiments of the invention, and although specific terms are employed, they are used in a generic and descriptive sense and not for purposes of limitation.

That which is claimed is:

1. A process of protecting seed from damage by corn wireworms, said process comprising
   (a) providing a liquid extract from a plant selected from the group consisting of butterfly milkweed, English ivy, santolina, bergamot, clary and swamp milkweed, said extract having no appreciable phytotoxicity to the, seed and
   (b) coating the seed with the extract to impart to the seed the feeding deterrency of the plant extract to protect thereby the seed when planted from damage by corn wireworms.

2. A process of protecting seed according to claim 1 wherein the step of providing the liquid extract comprises collecting specimens of the plant, homogenizing the collected plant specimens, and extracting liquid from the homogenate.

3. Seed produced by the process according to claim 1.

4. A process of protecting corn seed from damage by corn wireworms, said process comprising
   (a) providing a liquid extract from a plant selected from the group consisting of butterfly milkweed, English ivy, santolina, bergamot, clary and swamp milkweed, said extract having a natural feeding deterrency of predetermined efficacy to corn wireworms, and
   (b) coating the seed with said extract to impart to the seed the feeding deterrency of the liquid extract to protect thereby the seed when planted from damage by the corn wireworms, said extract having no appreciable phytotoxicity to said seed.

5. A process of protecting corn seed according to claim 4 wherein corn seed is coated with the liquid extract and including the further step of drying the coated seed at ambient temperature before planting thereof.

6. A process of protecting corn seed according to claim 4 wherein the step of providing the liquid extract comprises collecting specimens of the plant, homogenzing the collected plant specimens, and extracting liquid from the homogenate.

7. A process of protecting corn seed according to claim 6 wherein the plant specimens collected are selected from certain parts of the plant and are collected at such predetermined growth state of the plant as to avoid or minimize phytotoxicity.

8. Seed produced by the process according to claim 7.

9. Seed produced by the process according to claim 4.

10. A process of protecting corn seed from damage by corn wireworms and by Southern corn rootworms, said process comprising
    (a) providing a liquid extract from a plant selected from the group consisting of butterfly milkweed, English ivy and santolina, said extract having a natural feeding deterrency of predetermined efficacy to corn wireworms and Southern corn rootworms, and
    (b) coating the seed with said extract to impart to the seed the feeding deterrency of the liquid extract to protect thereby the seed when planted from damage by the corn wireworms and Southern corn rootworms, said extract having no appreciable phytotoxicity to said seed.

11. Seed protected from damage by corn wireworms, said seed comprising
    (a) seed that would be otherwise susceptible to damage by corn wireworms, and
    (b) a coating on said seed comprising a liquid extract from a plant selected from the group consisting of butterfly milkweed, English ivy, santolina, bergamot, clary and swamp milkweed, said extract having no appreciable phytotoxicity to said seed.

12. Seed according to claim 11 wherein said seed is corn seed.

13. Seed produced by the process according to claim 10.

14. A process of protecting seed from damage by corn wireworms and by Southern corn rootworms, said process comprising:
(a) providing a liquid extract from a plant selected from the group consisting of butterfly milkweed, English ivy and santolina, said extract having no appreciable phytotoxicity to said seed, and
(b) coating said seed with said extract to impart to the seed the feeding deterrancy of the plant extract to protect thereby the seed when planted from damage by corn wireworms and Southern corn rootworms.

15. A process of protecting seed as claimed in claim 14, wherein the step of providing the liquid plant extract comprises collecting specimens of the plant, homogenizing the collected plant specimens, and extracting liquid from the homogenate.

16. A process of protecting seed as claimed in claim 14, including the further step of drying the seed at ambient temperature before planting thereof.

17. A process of protecting seed as claimed in claim 14, wherein said seed is corn seed.

* * * * *